(12) United States Patent
Kanevsky et al.

(10) Patent No.: US 7,607,584 B2
(45) Date of Patent: Oct. 27, 2009

(54) VERIFICATION OF A BIOMETRIC IDENTIFICATION

(75) Inventors: Dimitri Kanevsky, Ossining, NY (US); Dmitri V. Talapin, Richmond, CA (US)

(73) Assignee: International Business Machines Corporation, Armonk, NY (US)

( * ) Notice: Subject to any disclaimer, the term of this patent is extended or adjusted under 35 U.S.C. 154(b) by 294 days.

(21) Appl. No.: 11/411,716

(22) Filed: Apr. 26, 2006

(65) Prior Publication Data

US 2007/0251996 A1  Nov. 1, 2007

(51) Int. Cl.
*G06K 19/06* (2006.01)
(52) U.S. Cl. ............... 235/491; 235/468
(58) Field of Classification Search ........ 235/556, 235/489, 491; 423/556, 489; 424/556, 489; 250/556, 489
See application file for complete search history.

(56) References Cited

U.S. PATENT DOCUMENTS

| | | | |
|---|---|---|---|
| 6,506,476 B1 * | 1/2003 | Kaule et al. | 428/195.1 |
| 2003/0025897 A1 * | 2/2003 | Iwai | 356/71 |
| 2003/0032192 A1 * | 2/2003 | Haubold et al. | 423/311 |
| 2005/0267345 A1 * | 12/2005 | Korgel et al. | 428/402.24 |
| 2006/0131517 A1 * | 6/2006 | Ross et al. | 250/556 |
| 2006/0269612 A1 * | 11/2006 | Xiang et al. | 424/489 |

* cited by examiner

*Primary Examiner*—Seung H Lee
*Assistant Examiner*—Christle I Marshall
(74) *Attorney, Agent, or Firm*—F. Chau & Associates, LLC

(57) ABSTRACT

An identification verification system includes a combination of indicia that represent measurable characteristics mapped into a characteristic signature, and an indicia detector for detecting the characteristic signature and verifying authenticity of the characteristic signature.

11 Claims, 6 Drawing Sheets

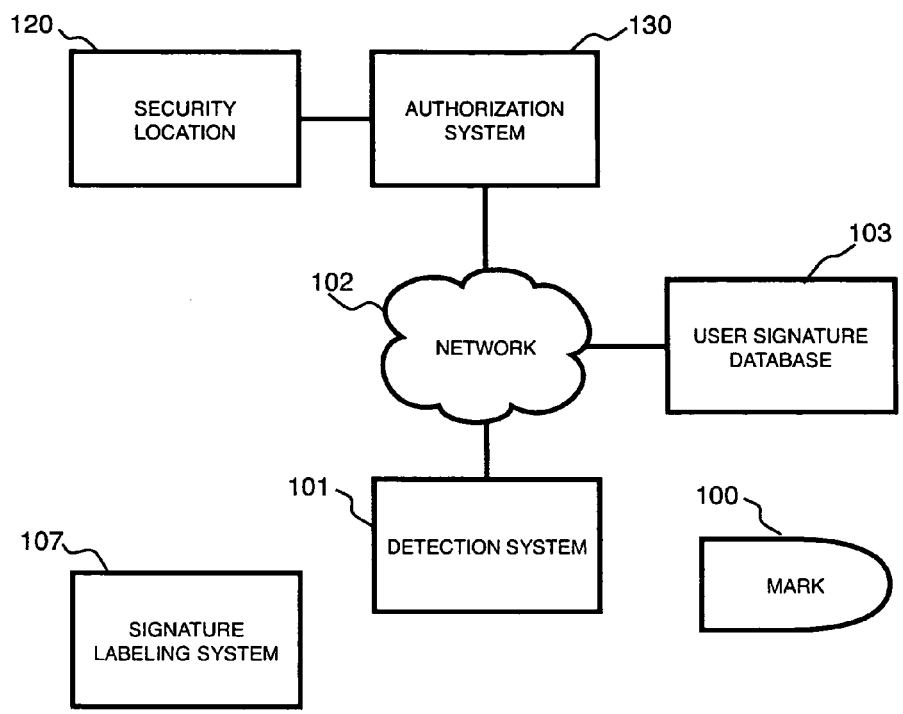
FIGURE 1
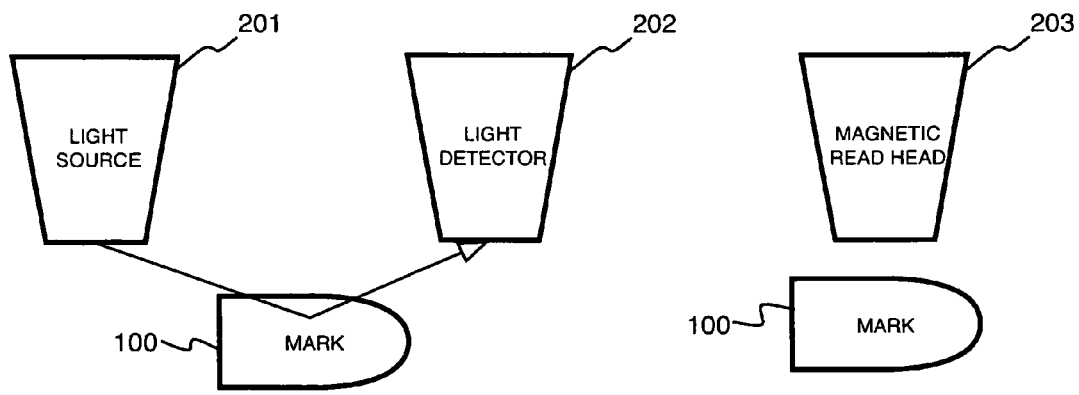
FIGURE 2A
FIGURE 2B

VERIFICATION OF A BIOMETRIC IDENTIFICATION

BACKGROUND OF THE INVENTION

1. Technical Field

The present invention relates to identity verification, and more particularly to a system and method for identification verification using small-scale indicia.

2. Discussion of Related Art

The verification of an individual to access a secured system is a difficult problem. Numerous systems for verification or authentication have been developed. These systems are not secure as could be desired.

Therefore, a need exists for a system and method for verification of identity.

SUMMARY OF THE INVENTION

According to an embodiment of the present disclosure, an identification verification system comprises a combination of indicia that represent measurable characteristics mapped into a characteristic signature, and an indicia detector for detecting the characteristic signature and verifying authenticity of the characteristic signature.

According to an embodiment of the present disclosure, an identification verification system comprises an indicia comprising a luminescent material, wherein the luminescent material exhibits up-conversion of light as a characteristic signature, a light source, and a light detector for detecting the indicia and verifying authenticity of the characteristic signature.

According to an embodiment of the present disclosure, an identification verification system comprises an indicia comprising magnetic particles, and an indicia detector reading information magnetically written in the indicia as a characteristic ferromagnetic resonance, and verifying authenticity of the indicia according to the characteristic ferromagnetic resonance.

BRIEF DESCRIPTION OF THE DRAWINGS

Preferred embodiments of the present disclosure will be described below in more detail, with reference to the accompanying drawings:

FIG. 1 is a diagram of a system according to an embodiment of the present disclosure;

FIG. 2A, is a diagram of a system implementing luminescent signatures according to an embodiment of the present disclosure;

FIG. 2B, is a diagram of a system implementing magnetic signatures according to an embodiment of the present disclosure;

DETAILED DESCRIPTION OF PREFERRED EMBODIMENTS

Figure 2C:
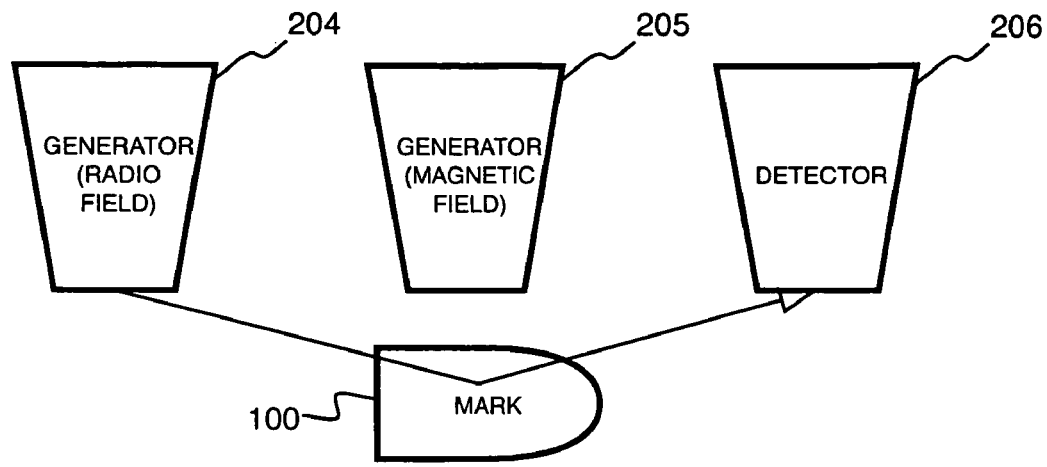
FIG. 2C, is a diagram of a system implementing radio frequency signatures according to an embodiment of the present disclosure.

According to an embodiment of the present disclosure, an identifier is formed on a small-scale (molecular or nano-scale) in a liquid or other material such as an enamel. These materials, used as identification, can be applied to skin, nails, etc., or other substrates, e.g., dress, jewelry, documents. Identifying features or indicia can be verified by a security sensor system. The indicia are embodied in luminescent or magnetic materials, or both.

Examples of luminescent indicia include luminescent dye molecules, luminescent semiconductor indicia, phosphors, combinations of luminescent indicia, etc. Examples of magnetic indicia include materials exhibiting ferromagnetic resonance and the like.

Luminescent particles generate light with a characteristic wavelength and life-time. Both these parameters depend on the particle size, shape and material. This light is generated upon excitation with light of a characteristic wavelength. One can convert into bits the emission wavelength, the spectral width, the emission life-time, the excitation wavelength, etc. Moreover, one can use a mixture of luminescent particles to increase the number of bits.

Luminescent dye molecules (e.g., flourescein, quinine, perylene, rhodamine 6G, etc.) emitting in different spectral regions (e.g., blue, green, yellow, red, near-IR) and combinations thereof can be dissolved in an appropriate liquid (e.g., ethyl acetate) and put into a material such as a nail varnish. Detection of the luminescent dye molecules is based on excitation by light (e.g., ultra-violet (UV) light) and detection of specific dye luminescence. For example, rhodamine 6G molecules emit light at a wavelength of about 550 nm upon excitation by UV light with a wavelength of about 350 nm.

Referring to luminescent semiconductor indicia; these indicia implement any of a class of materials including small pieces of semiconducting materials (e.g., silicon (Si), cadmium selenide (CdSe), cadmium telluride (CdTe), indium phosphide (InP), zinc selenide (ZnSe), etc.) with physical sizes between about 1 nm and 15 nm, capped with shells of organic ligands. The band gaps of the semiconductor indicia and, in turn, the emission wavelengths, depend on the particle size due to quantum confinement effects. Emission wavelength of semiconductor indicia can be tuned through the visible spectral range and near-IR by varying particle size and chemical composition. The shell of organic ligands makes luminescent indicia soluble in a desired solvent (e.g., polar solvents like water of non-polar solvents like hexane). Luminescent properties of semiconductor indicia can be substantially improved if the emitting core of a nano-particle is protected by the shell of a wide band-gap semiconductor (core-shell indicia, e.g. CdSe/ZnS (zinc sulfide), CdSe/CdS (cadmium sulfide), etc.). The core-shell indicia can be dispersed in an appropriate liquid carrier and used as luminescent indicia analogous to the dye molecules. Semiconductor indicia offer improved stability, better purity of the emission color, and a unique possibility of simultaneous excitation of indicia emitting in different spectral regions over dye molecules. For example, core/shell CdSe/ZnS indicia capped with hexadecylamine-trioctylphosphine ligand shell can be dispersed in a non-polar solvent like hexane. The particle luminescence can be excited by a UV light source. Emission of indicia depends on size of CdSe core (~3 nm—green, ~4.5 nm—yellow, ~6 nm—red).

Referring now to phosphores, colloidal indicia doped with rare-earth elements (e.g., $YVO_4$:Ln (Ln=Eu, Sm, Dy), $LaPO_4$:Eu, LaPO4:Ce, $LaPO_4$:Ce, Tb indicia). These indicia can be dispersed in an appropriate solvent like dye molecules or semiconductor indicia. Luminescence of these indicia is generated by electron transition between the characteristic f-levels of rare-earth doping atoms. The luminescent indicia generate characteristic emission spectrum including several narrow lines at characteristic wavelengths, and high stability of luminescent properties. The luminescent properties of rare-earth doped indicia can be further improved for growing core/shell indicia (e.g., $CePO_4$:Tb/$LaPO_4$ Core-Shell Indicia). For example, 5 nm $LaPO_4$:Ce,Tb indicia stabilized by tris(ethylhexyl)phosphate can be dispersed in ethanol, methanol, 2-propanol or ethyl acetate. Luminescence of $LaPO_4$:Ce, Tb indicia can be excited at 275 nm. The emission spectrum includes a series of characteristic lines with the most intense line at 542 nm. The lanthanide-doped $NaYF_4$ crystals can be used in luminescent security indicia based on photon up-conversion. Photon up-conversion is the generation of visible radiation by near-IR excitation. It is based on sequential absorption of several (two) photons transferring energy to a single emitted photon. This effect is very rare in nature, providing very high level of security. Examples: ~10 nm $NaYF_4$: 20% Yb, 2% Er indicia being excited by invisible near-IR (10270 $cm^{-1}$) light emit visible green and red light while NaYF4:20% Yb, 2% Tm indicia being excited by invisible near-IR (10270 $cm^{-1}$) light emit blue light.

Combinations of luminescent indicia emitting in different spectral regions can be used in multicolor indicia.

In addition to continuous luminescence, the security mark can be detected by luminescence lifetime. Luminescence lifetime is characteristic for different types of materials (dye molecules, semiconductor indicia, rare-earth doped indicia).

Magnetic indicia can be implemented as a magnetic material dispersed in a solvent and used as media for magnetic data recording. The detection of the magnetic indicia can be based on reading information magnetically written on the layer of magnetic material.

The use of magnetic indicia allows achieving high density of data recording, for example, 100 Gbits/$inch^2$. Information can be written on the film of magnetic particles in a manner similar to magnetic tapes or credit cards. The particles can potentially provide very high writing density (up to 1 Tbite per square inch).

Magnetic indicia can be embodied as a material exhibiting ferromagnetic resonance. Ferromagnetic materials, e.g., Co, Fe, $Fe_2O_3$, $CoFe_2O_4$, FePt, etc. exhibit magnetic susceptibility, which is the magnetic response or the degree of magnetization of a material in response to a magnetic field. An extension of magnetic marks are ferromagnetic marks. The information borne by a ferromagnetic mark is the characteristic resonant response to a high-frequency low-power magnetic excitation (dynamical susceptibility). Resonance field and line width depend on effective magnetic anisotropy, relaxation time of the magnetization, and other parameters of the indicia material used as security labels. Additionally, marnetic response depends on the the particle size and shape. Combination of indicia of different materials or indicia of the same material but of different size can generate a complex magnetic response for increasing a level of security.

Quantum effects can be unique for different materials; the size quantization of electronic structure and magnetic properties of materials can be used as indicia.

According to the examples set forth herein, indicia can be used for security labels.

An exemplary implementation can include optical/luminescent labels using indicia arranged as a bar code. Such a bar code can use combinations of indicia and luminescent dyes. The materials can be used in form of indicia.

Indicia comprised of semiconductor particles behaving as quantum dots provide a narrow emission peak having a spectral position that depends on the particle size. Further, phosphores can be implemented. Phosphores generate several lines with relative intensities characteristic to the material. Intensities of several emission lines can be detected using several band-pass optical filters. Such an arrangement can be used in a detection system. Relative intensities of emission lines can be used in the detection of an identifying mark, wherein the intensity of two different emission peaks are detected and compared.

Up-conversion detection can be implemented using luminescent indicia. The up-converting materials will excite in infrared light, and generate characteristic visible light. There are several materials that can do this including for example, GaAs/AlGaAs structures (for up-conversion of 980 nm light into 850 nm light or $Yb^{3+}$ ion-doped oxyfluoride vitroceramic material (Yb:FOV) (for up-conversion blue luminescence).

These materials can show unique physical properties (e.g., they can illuminate). Biological tagging can be used to follow certain biological processes.

A mixture of biometrics and tagging identification can be implemented. For example, tag indicia are put on a finger and a joint picture of a fingerprint and indicia can be produced.

The indicia can be a permanent marking element. An extension of the permanent marking is a time-decaying indicia. Gradual changes in properties of indicia material, for example, luminescence efficiency of some kinds of nanocrystals (e.g., CdTe), can decay in time due to oxidation of crystals in air. This provides a solution for security indicia that are operational for certain period of time and deactivate themselves when this period is over.

Multiple indicia may be used as part of a combined indicia, using in an identification process to verify the multiple indicia.

Spray on indicia can be implemented over areas.

The particles can be embedded in other objects to provide the identification function. Instead of being on the nail polish, it would be something that is applied to the surface of a ring or someone's tie or many other objects. They can provide an invisible and simple means of detection.

The materials that present a signal can be detected by some range of means including optical detection and magnetic detection.

The materials can be adjusted by these types of quantum effects.

Regarding indicia having a decay function, the decay or evolution is the disappearance of the indicia over time. The indicia can be adjusted to function for a limited period. The materials may exhibit this time evolution that may be controlled according to a sensitivity and size of the indicia. Single long wavelength radiation converted to be invisible. This leads to other types of detection methods. These materials, because of their properties, can be modified by one interact with radiation that then makes them susceptible to interaction with another form of radiation; the materials have a transitional sensitized state. For example, phosphorus may not immediately emit light upon illumination, but upon infrared with red light, a mark comprising phosphorus is detectable. A single use detection mode implements such a phosphorus indicia, wherein information is destroyed by a read method.

Referring to FIG. 1, a mark 100, such as nail that is covered with a nail varnish or a ring, includes indicia representing an access code, for example, for gaining access to a secure location or document. A mark may be repeatedly generated for granting a group access, for example, a department of a company has access to a particular room.

A detector system 101 comprises a detector sensor for reading the mark 100. Read data is converted into a string of bits (e.g., an analog to digital conversion) that is communicated via a network 102 to a user signature database 103. The user signature database 103 provides the data to the authorization system 130.

The authorization system 130 can return a response to the detection system 101, for example, indicating whether a password was found, and/or an indication of the reliability of the data (e.g., data read from the mark may be corrupted; the reliability of the data can be determined by measuring how many bits in the data correspond to a stored user signature or template).

Referring to FIG. 2A a mark 100 comprising luminescent particle labels is illuminated by a light source 201. A light detector 202 of the detection system 101 measures light intensity at specific wavelengths. Optionally, the light source 201 produces a pulsed excitation light, and light detector 202 measures a luminescence life-time, characteristic to the mark 101.

Referring to FIG. 2B a detector comprises a magnetic read head 203 for reading information magnetically written to a layer of particles, e.g., ferromagnetic particles arranged in a strip.

Referring to FIG. 2C a detector 206 measures the power of radio-frequency radiation absorbed by particles. Radio-frequency radiation is generated by generator 204. A magnetic field generator 205 produces magnetic field of variable strength. Under characteristic magnetic fields magnetic particles show strong absorption of radio-frequency radiation (conditions of ferromagnetic resonance).

Figure 3:
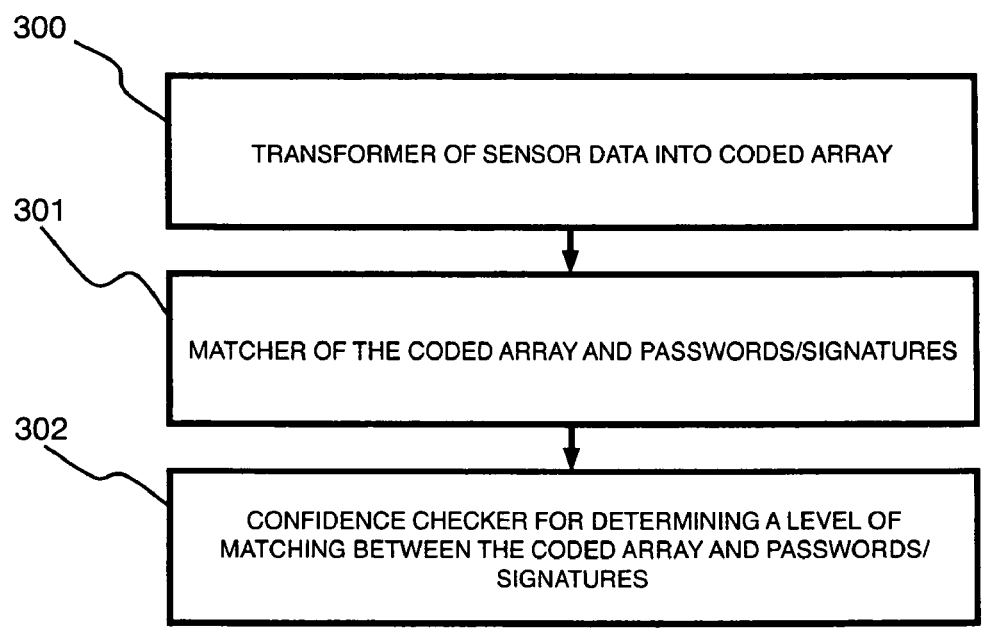
FIG. 3 is a diagram of a signature verification system according to an embodiment of the present disclosure.

Referring to FIG. 3 and the detection system 101; a transformer 300 converts sensor data into a coded array, e.g., in a format following a special protocol. For example a ratio of certain components of different materials is represented as a string of bits of certain length. A matcher 301 of the coded array compares the coded array with passwords stored in the signature database 103. One or more matched signatures are chosen. A Different metrics can be used to measure distances between the bits of a coded array received from the transformer 300 and signatures that are stored in signature database 103. For example, Euclidean metrics (e.g., that determine distances between points in Euclidean vector spaces) are used to determine how many positions are different between the array code and the reference in the signature database 103, adjusted with statistical weights for reliability. For example, lower decimal numbers in the ratio of the marks can have lower confidence scores. A confidence checker 302 determines a level of matching between the entry code array and the one or more matched signatures from the database.

Information determined by the transformer 300, matcher 301 and confidence checker 302 is used in the authorization system 130 to decide whether to accept the mark or whether additional processes are needed to check an identity of a bearer of the mark.

Figure 4:
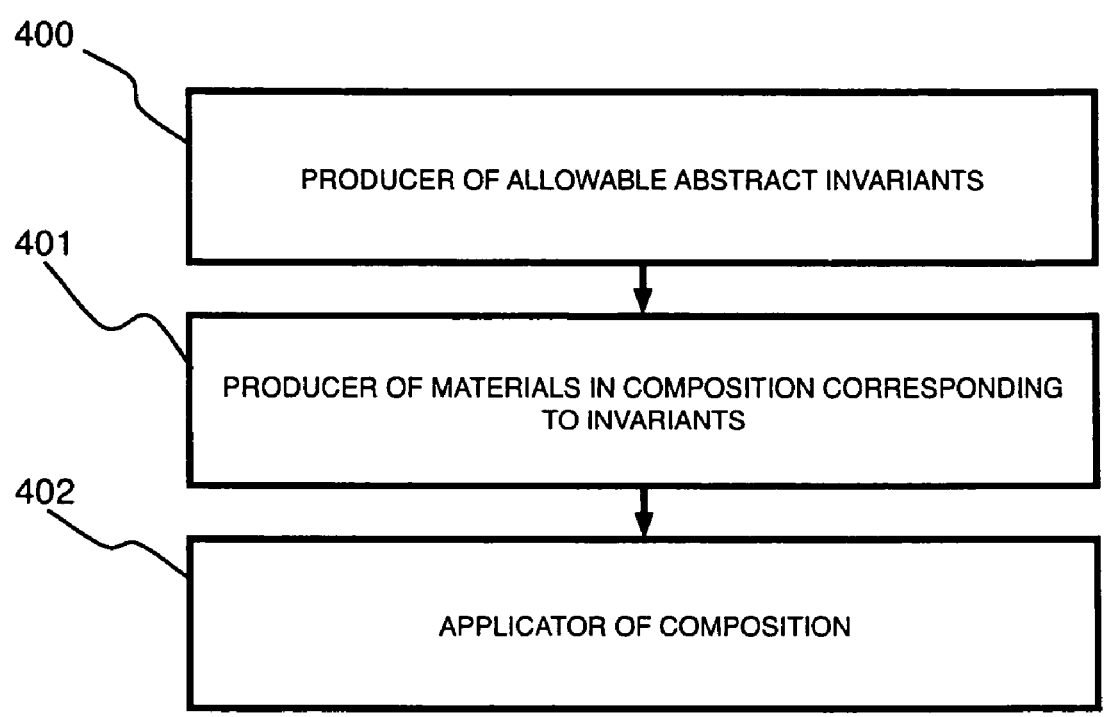
FIG. 4 is a diagram of a signature labeling system according to an embodiment of the present disclosure.

Referring to FIG. 4 and a mark generation system includes a produce of invariants 400, a producer of materials in composition corresponding to the invariants 401 and an applicator 402. A producer of allowable abstract invariants 400 (like a coded array) represents, mathematically, invariant properties that can be reproduced as physical substances and that can represent sufficient number of bits for a password protection method, e.g., unique passwords different from already stored passwords. A producer of particles 401 is provided for producing a composition that corresponds to invariants from the producer of invariants 400. An applicator 402 is provided that puts structures from the producer of particles 401 onto/into a carrier (e.g., a liquid carrier) in order that they can be used later to apply a signature.

Figure 5:
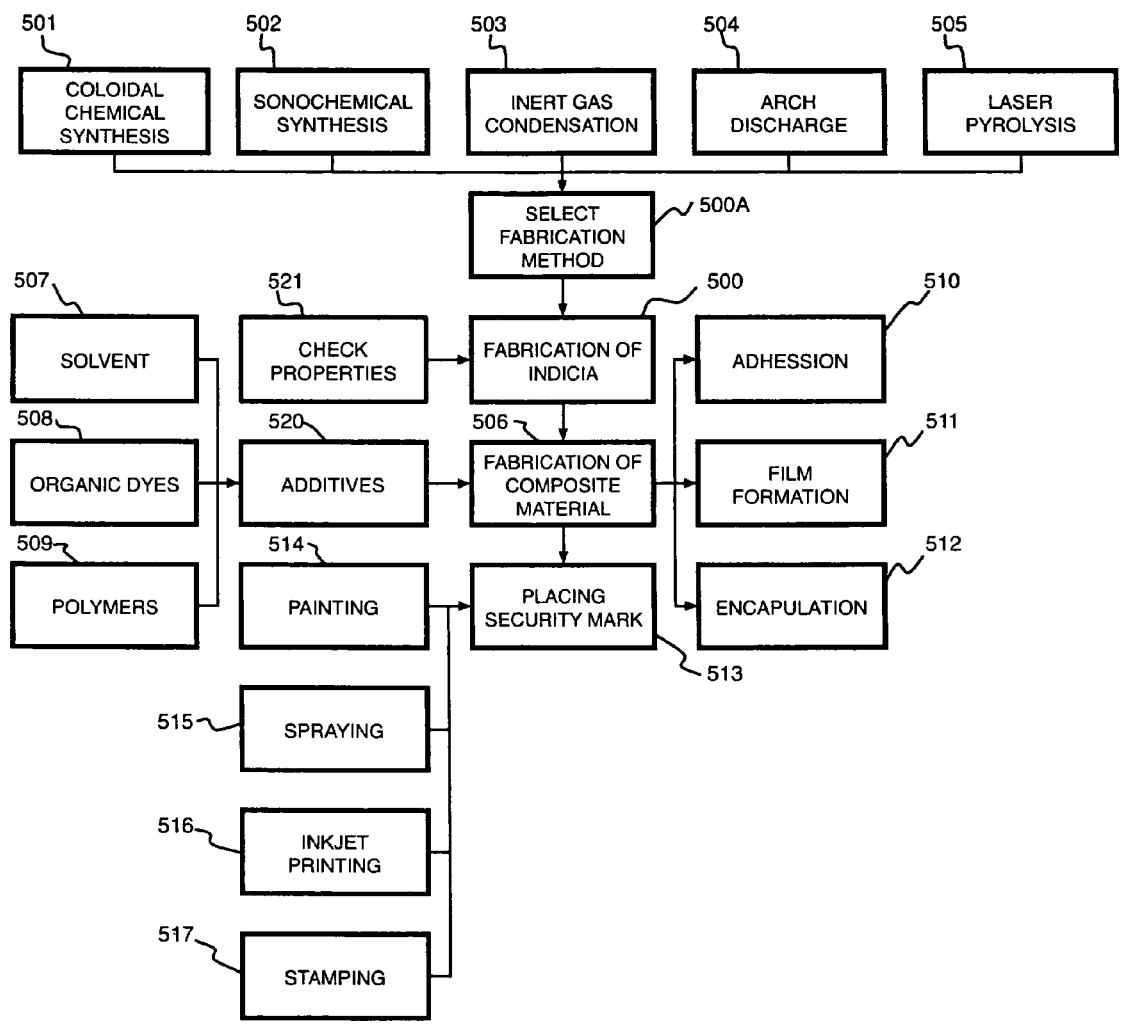
FIG. 5 is a flow chart of a method according to an embodiment of the present disclosure.

Referring to FIG. 5, a method for creating unique identification properties of signatures (e.g., combination of particles, materials as particles, emission of spectra, intensity, invisible means, quantum effects, precision etc.) comprises fabricating indicia 500 with unique luminescent or magnetic signatures. The indicia in form of semiconductor, phosphor of magnetic nanoparticles can be fabricated by means of colloidal chemical syntheses 501. Alternatively, nanoparticles can be fabricated by sonochemical synthesis 502, inert gas condensation 503, arc discharge 504, laser pyrolysis 505, etc. A composite material with desired luminescent or magnetic signature is prepared by mixing different nanoparticles 506. Additives such as solvents 507, organic dyes 508, and polymers 509 can be added 520 to the composite material to provide desired physical and chemical properties 521 such as adhesion 510, film formation 511, encapsulation 512, etc. to the security mark. The security mark can be placed 513 on a desired surface (e.g., human nail) using different techniques such as painting 514, spraying 515, inkjet printing 516, stamping 517, etc.

Figure 6:
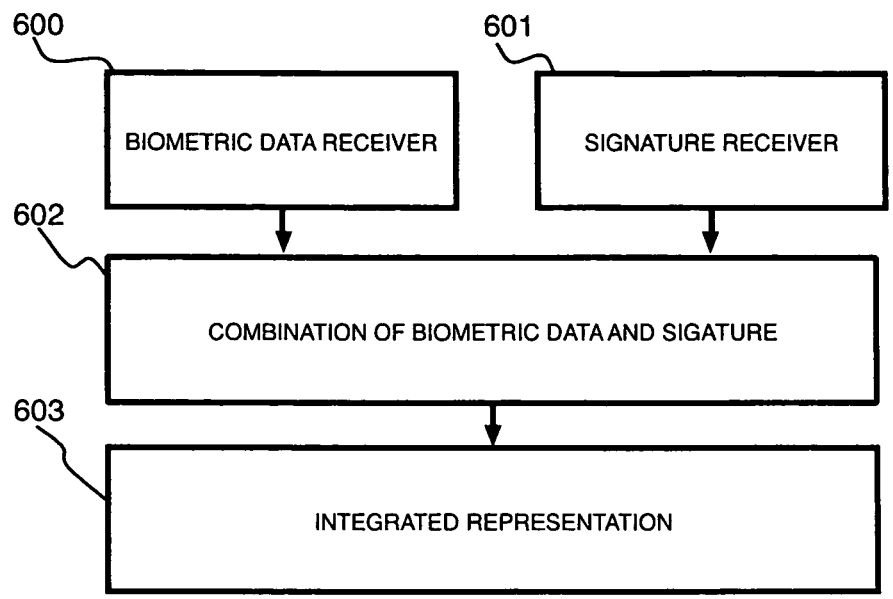
FIG. 6 is a diagram of an identification verification system implementing multiple security checks according to an embodiment of the present disclosure.

Referring to FIG. 6 and the integration of biometrics and signatures; biometrics and signature integration increases the level for confidence one can have in a security indicia. For example, putting patterns on a finger in a unique way. This adds to a fingerprint some additional information that provides an additional level of security. This could be helpful to distinct identical twins.

A biometric data receiver 600, for example, can receive fingerprints and represent them in some digital form (like pins in a vector space of various intensity).

A nano signature receiver 601 represents signatures in some digital form (like a code array). It represents signatures as some array by reading data from a material that contain biometrics and materials and representing structures (how are the located relatively to biometrics and their composition). For example, how particles are located relatively to fingerprint characteristics.

The block 602 gives in digital form representation how biometrics and characteristics are interrelated (for example, how particles are located relatively fingerprint pins of different intensity and positions).

In the block 603 these mixed characteristics are represented in some integrated mathematical form that put biometrics and correlated information as some classes of data. This is needed since particles cannot be put exactly on a living body parts with high accuracy. There is some degree uncertainity and therefore the classification is needed like a spot of some material and of some intensity that is located in upper left part of a finger.

Figure 7:
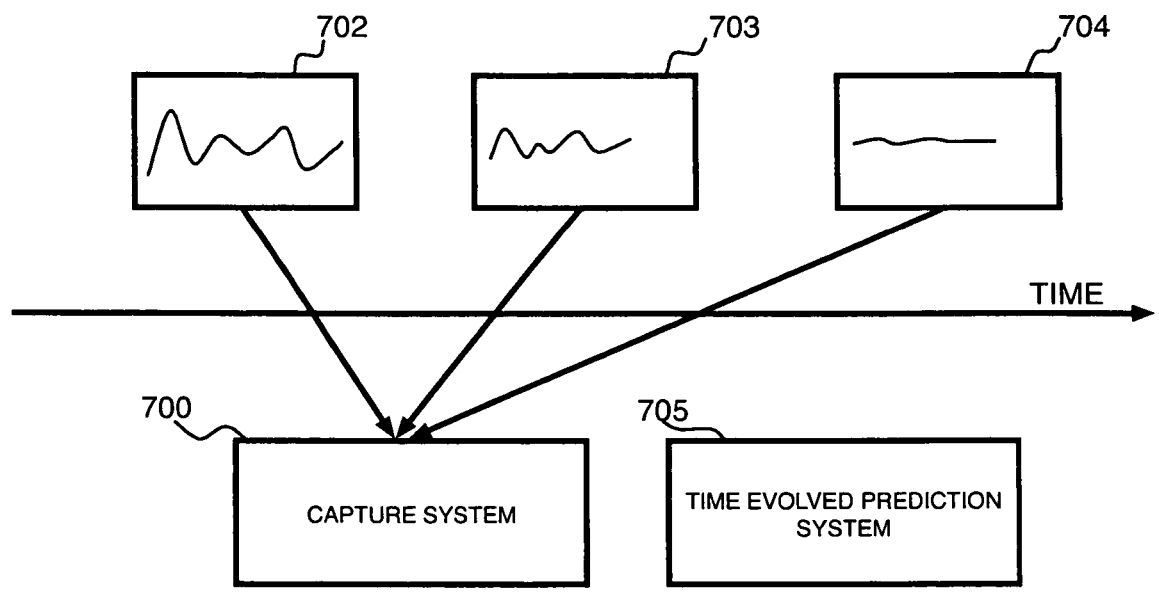
FIG. 7 is an illustration of a time-decay system according to an embodiment of the present disclosure.

Referring to FIG. 7 and the evolving of signatures with time; Block 700 (that belongs to the detection system 103) captures signature related information from sensors 101. Signature shots in different times 701 are shown in 702, 703 and 704. These signature shots are compared with known evolution properties for signature prototypes 705 that are stored in the user signature database 105.

Figure 8:
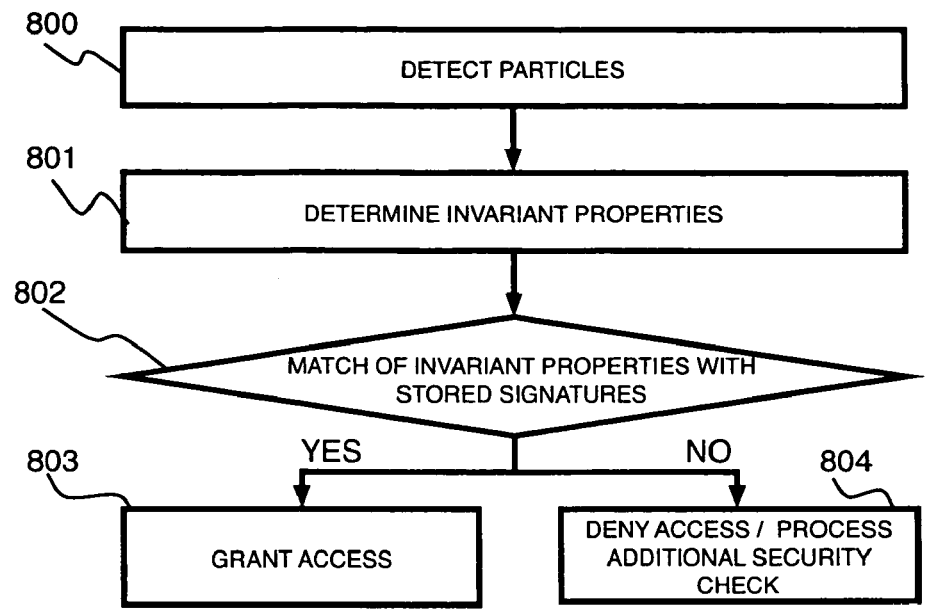
FIG. 8 is a flow chart of a method according to an embodiment of the present disclosure.

Referring to FIG. 8, a method includes detection of indicia 800, the determination of properties invariants (like composition of materials, time dependent characteristics etc.) 801, determining whether there is a "good" match between the detected nano properties invariants and stored prototype invariants 802 and, if the answer is "Yes" then grant security access 803 otherwise—deny access or process additional security checks 804.

Exemplary implementations include a) "Nanophosphores"—colloidal particles doped with rare-earth elements. These materials have some obvious advantages over semiconductor particles (quantum dots): (i) very characteristic emission spectrum including several narrow lines at characteristic wavelengths with characteristic intensity ratio making them very difficult to counterfeit; (ii) High stability and robustness of luminescent properties.

b) Security indicia utilizing luminescence up-conversion. The rare-earth doped $NaYF_4$ colloidal nanoparticles: generation of visible radiation by near-IR excitation. This effect is very rare in nature, providing very high level of security.

c) Magnetic particles as security indicia with the detection principle based on reading information magnetically written on the layer of magnetic particles or on the effect of ferromagnetic resonance.

d) Combination of different security indicia (luminescent, magnetic, etc.)

e) Natural dynamic changes of signatures with time patterns for changing properties as way to verify that this is a right verification process f) Integration on signature with natural biometrics and using this as a bio-verification (for example, spraying on a finger and including finger prints and particles to create a unique verification image)

g) spray distributes security labeling over large parts of body and this way preventing such events as cutting a finger with a security label for identification.

h) Using spray to label large groups of visitors with the same security labels cost effectively and quickly.

It is to be understood that the present invention may be implemented in various forms of hardware, software, firmware, special purpose processors, or a combination thereof. In one embodiment, the present invention may be implemented in software as an application program tangibly embodied on a program storage device. The application program, e.g., mark detection software, database software, etc., may be uploaded to, and executed by, a machine comprising any suitable architecture.

Figure 9:
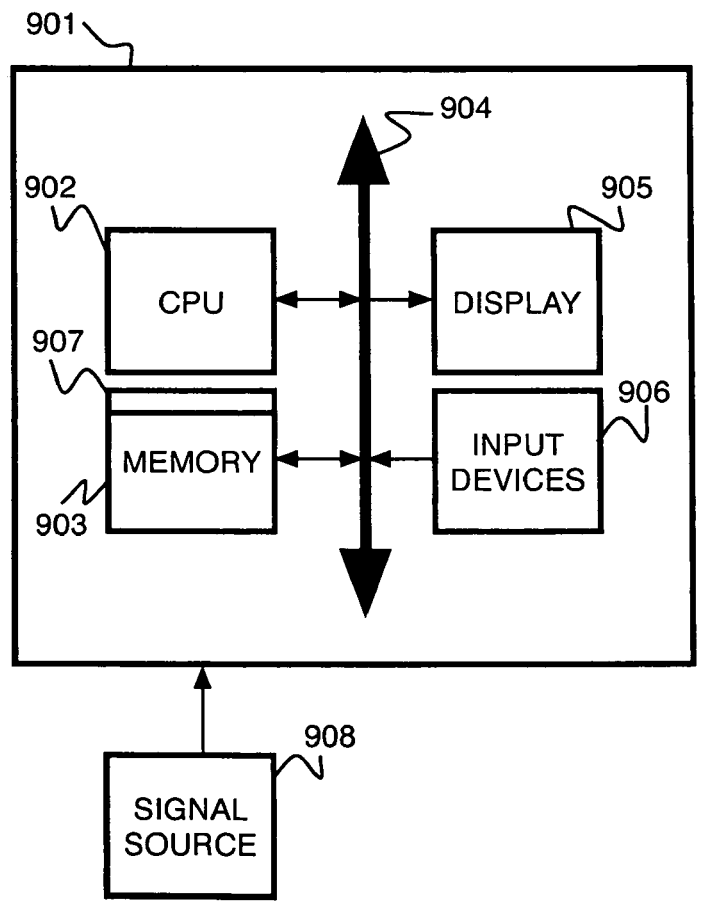
FIG. 9 is a diagram of a system according to an embodiment of the present disclosure.

Referring to FIG. 9, according to an embodiment of the present invention, a computer system 901 for implementing the present invention can comprise, inter alia, a central processing unit (CPU) 902, a memory 903 and an input/output (I/O) interface 904. The computer system 901 is generally coupled through the I/O interface 904 to a display 905 and various input devices 906 such as a mouse and keyboard. The support circuits can include circuits such as cache, power supplies, clock circuits, and a communications bus. The memory 903 can include random access memory (RAM), read only memory (ROM), disk drive, tape drive, etc., or a combination thereof. The present invention can be implemented as a routine 907 that is stored in memory 903 and executed by the CPU 902 to process the signal from the signal source 908. As such, the computer system 901 is a general purpose computer system that becomes a specific purpose computer system when executing the routine 907 of the present invention.

The computer platform 901 also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Having described embodiments for a system and method for verification of a biometric identification, it is noted that modifications and variations can be made by persons skilled in the art in light of the above teachings. It is therefore to be understood that changes may be made in particular embodiments of the invention disclosed which are within the scope and spirit of the disclosure.

What is claimed is:

1. An identity verification system comprising:
   a combination of indicia that represents measurable characteristics mapped into a characteristic signature, wherein the measurable characteristics comprise a luminescent characteristic and a biometric characteristic, wherein the biometric characteristic is integrated with the luminescent characteristic to create a unique verification image; and
   an indicia detector for detecting the characteristic signature and verifying authenticity of the characteristic signature,
   wherein the combination of indicia comprises colloidal nanoparticles having a characteristic emission spectrum comprising a plurality of lines at characteristic wavelengths with characteristic intensity ratio, wherein the indicia detector detects the characteristic emission spectrum.

2. The identity verification system of claim 1, further comprising a database of indicia, wherein the indicia detector compares the characteristic emission spectrum to the database of indicia having corresponding characteristic emission spectrum to determine a security level associated with the indicia.

3. The identity verification system of claim 1, wherein the measurable characteristics are invariant.

4. The identity verification system of claim 1, wherein the indicia comprises a sprayed layer over an area.

5. The identity verification system of claim 1, wherein the indicia comprises a sprayed layer over a plurality of substrates.

6. The identity verification system of claim 1,
   wherein the measurable characteristics include adsorption of radio-frequency radiation, the identity verification system further comprising:
   a radio field generator; and
   a magnetic field generator for producing a magnetic field affecting the indicia, a portion of the radio-frequency radiation being absorbed by the indicia affected by the magnetic field, wherein the absorbed portion of the radio-frequency radiation is the characteristic signature.

7. An identity verification system comprising:
   a combination of indicia that represents measurable characteristics mapped into a characteristic signature, wherein the measurable characteristics comprise a luminescent characteristic and a biometric characteristic, wherein the biometric characteristic is integrated with the luminescent characteristic to create a unique verification image; and an indicia detector for detecting the characteristic signature and verifying authenticity of the characteristic signature, wherein the indicia has a known time-decay characteristic.

8. The identity verification system of claim 7, wherein the measurable characteristics are invariant.

9. The identity verification system of claim 7, wherein the indicia comprises a sprayed layer over an area.

10. The identity verification system of claim 7, wherein the indicia comprises a sprayed layer over a plurality of substrates.

11. The identity verification system of claim 7, wherein the measurable characteristics include adsorption of radio-frequency radiation, the identity verification system further comprising:

a radio field generator; and a magnetic field generator for producing a magnetic field affecting the indicia, a portion of the radio-frequency radiation being absorbed by the indicia affected by the magnetic field, wherein the absorbed portion of the radio-frequency radiation is the characteristic signature.

* * * * *

UNITED STATES PATENT AND TRADEMARK OFFICE
CERTIFICATE OF CORRECTION

PATENT NO. : 7,607,584 B2  Page 1 of 1
APPLICATION NO. : 11/411716
DATED : October 27, 2009
INVENTOR(S) : Kanevsky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 478 days.

Signed and Sealed this

Twelfth Day of October, 2010

David J. Kappos
*Director of the United States Patent and Trademark Office*